United States Patent
Noteborn

(10) Patent No.: US 6,620,925 B1
(45) Date of Patent: Sep. 16, 2003

(54) METHODS AND MEANS FOR INDUCING APOPTOSIS BY INTERFERENCE IN RNA PROCESSING

(75) Inventor: M. H. M. Noteborn, Leiderdorp (NL)

(73) Assignee: Leadd B.V., Leiden (NL)

(*) Notice: Subject to any disclaimer, the term of this patent is extended or adjusted under 35 U.S.C. 154(b) by 0 days.

(21) Appl. No.: 09/452,846

(22) Filed: Dec. 3, 1999

(51) Int. Cl.[7] .................. C07H 21/04; C07H 21/02; C12N 15/00
(52) U.S. Cl. ............. 536/23.5; 536/23.1; 536/24.5; 435/320.1
(58) Field of Search ................ 536/23.1, 24.5, 536/23.5; 435/320.1

(56) References Cited

FOREIGN PATENT DOCUMENTS

| EP | 0924296 A2 * | 6/1999 |
|---|---|---|
| WO | WO 98/08965 | 3/1998 |

OTHER PUBLICATIONS

Hillier et al. (Genbank, EST database, Accession No. AA773455, Jan. 29, 1998.).*
Witte et al. (Proc.Natl.Acad.Sci. vol. 94, pp. 1212–1217, Feb. 1997).*
Harris et al., J. of The Am Society of Nephrology 6:1125–33, 1995.*
Ahn et al., Nature Genetics 3(4):283–91, 1993.*
Cawthon et al., Genomics 9(3):446–60, 1991.*
Oorschot et al. (Proc.Natl.Acad.Sci. vol. 94, pp. 5843–5847, May 1997).*
Casciola–Rosen, Livia A. et al., Specific Cleavage of the 70–kDa Protein Component of the U1 Small Nuclear Ribonucleoprotein Is a Characteristic Biochemical Feature of Apoptotic Cell Death, The Journal of Biological Chemistry, 1994, pp. 30757–30760, vol. 269. No. 49, The American Society for Biochemistry and Molecular Biology, Inc., US.
Honore, Bent et al., Heterogeneous Nuclear Ribonucleoproteins H, H', anf F Are Members of a Ubiquitously Expressed Subfamily of Related but Distinct Proteins Encoded by Genes Mapping to Different Chromosomes, The Journal of Biological Chemistry, 1995, pp. 28780–28789, vol. 270. No. 48. The American Society for Biochemistry and Molecular Biology, Inc.
Partial European Search Report, EP 98 20 4089.
Zhuang, Shi–Mei et al., Apoptin, a Protein Derived from Chicken Anemia Virus, Induces p53– independent Apoptosis in Human Osteosarcoma Cells, Cancer Research, Feb. 1, 1995, pp. 486–489, vol. 55, No. 3.

* cited by examiner

Primary Examiner—Anthony C. Caputa
Assistant Examiner—Gary B. Nickol
(74) Attorney, Agent, or Firm—TraskBritt

(57) ABSTRACT

The invention relates to activation of apoptosis by means of interference with the function of snRNPs and hnRNP-like compounds.

Also the invention relates to anti-tumor therapies with compounds, which negatively interfere with snRNPs and hnRNP-like compounds leading to induction of apoptosis, resulting in the elimination of tumor cells.

Also the invention relates to therapies for diseases related to aberrant apoptosis induction, such as auto-immune diseases.

16 Claims, No Drawings

SEQUENCE LISTING

<160> NUMBER OF SEQ ID NOS: 7

<210> SEQ ID NO 1
<211> LENGTH: 650

-continued

```
<212> TYPE: DNA
<213> ORGANISM: Homo sapiens
<220> FEATURE:
<221> NAME/KEY: misc_feature
<223> OTHER INFORMATION: /note="hnRNP-clone"
<221> NAME/KEY: variation
<222> LOCATION: (90)..(644)
<223> OTHER INFORMATION: n can be any nucleotide

<400> SEQUENCE: 1
ctgaaaatga cattgctaat ttcttctcac cactaaatcc aatacgagtt catattgata     60
ttggagctga tggcagagcc acaggagaan cnccntgtag agtttgtgac acatgaagat    120
gcagtagctg ccatgtctaa agataaaaat aacatgcaac atcgatatat tgaactcttc    180
ttgaattcta ctcctggagg cggctctggc atgggaggtt ctggaatggg aggctacgga    240
agagatggaa tggataatca gggaggctat ggatcagttg aagaatggga atggggaac     300 aattacagtg gaggatatgg tactcctgat ggtttgggtg ttatggccg tggtggtgga     360 ggcagtggag gttactatgg gcanngcggc atgagtggag gtggatggcg tgggatgtac    420
tgaaagcaaa acaccaaca tacaagtctt gacaacagca tctggtctac tagactttct     480
tacagattta atttcttttg tattttaaga actttataat gactgaagga atgtgttttc    540
aanatattat ttgngaaagc aacagattgt gatgggaaaa tgtttcngt tagtttattt     600 gttgcatacc ttgacttaaa aataaatttt atattcaaac cnnnaaattg                650

<210> SEQ ID NO 2
<211> LENGTH: 214
<212> TYPE: PRT
<213> ORGANISM: Homo sapiens
<220> FEATURE:
<221> NAME/KEY: misc_feature
<223> OTHER INFORMATION: /note="Amino acid sequence of hnRNP-clone"
<221> NAME/KEY: variation
<222> LOCATION: (34)..(213)
<223> OTHER INFORMATION: Xaa can be any amino acid

<400> SEQUENCE: 2

His Glu Gly Pro Glu Asn Asp Ile Ala Asn Phe Phe Ser Pro Leu Asn
 1               5                  10                  15

Pro Ile Arg Val His Ile Asp Ile Gly Ala Asp Gly Arg Ala Thr Gly
                20                  25                  30

Glu Xaa Pro Val Glu Phe Val Thr His Glu Asp Ala Val Ala Ala Met
            35                  40                  45

Ser Lys Asp Lys Asn Asn Met Gln His Arg Tyr Ile Glu Leu Phe Leu
    50                  55                  60

Asn Ser Thr Pro Glu Ala Ala Leu Ala Trp Glu Val Leu Glu Trp Glu
65                  70                  75                  80

Ala Thr Glu Glu Met Glu Trp Ile Ile Arg Glu Ala Met Ile Ser Trp
                85                  90                  95

Lys Asn Gly Asn Gly Glu Gln Leu Gln Trp Arg Ile Trp Tyr Ser Trp
            100                 105                 110

Phe Gly Trp Leu Trp Arg Gly Gly Gly Ser Gly Tyr Tyr Gly
        115                 120                 125

Xaa Xaa Gly Met Ser Gly Gly Gly Trp Arg Gly Met Tyr Ser Lys Asn
    130                 135                 140

Thr Asn Ile Gln Val Leu Thr Thr Ala Ser Gly Leu Leu Asp Phe Leu
145                 150                 155                 160

Thr Asp Leu Ile Ser Phe Tyr Phe Lys Asn Phe Ile Met Thr Glu Gly
                165                 170                 175
```

```
Met Cys Phe Gln Xaa Ile Ile Xaa Glu Ser Asn Arg Leu Trp Lys Met
            180                 185                 190

Phe Ser Val Ser Leu Phe Val Ala Tyr Leu Asp Leu Lys Ile Asn Phe
        195                 200                 205

Ile Phe Lys Pro Xaa Asn
    210

<210> SEQ ID NO 3
<211> LENGTH: 199
<212> TYPE: PRT
<213> ORGANISM: Homo sapiens
<220> FEATURE:
<221> NAME/KEY: misc_feature
<223> OTHER INFORMATION: /note="Amino acid sequence of hnRNP-clone"

<400> SEQUENCE: 3

Asp Gly Tyr Gly Phe Gly Ser Asp Arg Phe Gly Arg Asp Leu Asn Tyr
1               5                   10                  15

Cys Phe Ser Gly Met Ser Asp His Arg Tyr Gly Asp Gly Gly Ser Thr
            20                  25                  30

Phe Gln Ser Thr Thr Gly His Cys Val His Met Arg Gly Leu Pro Tyr
        35                  40                  45

Arg Ala Thr Glu Asn Asp Ile Tyr Asn Phe Phe Ser Pro Leu Asn Pro
    50                  55                  60

Val Arg Val His Ile Glu Ile Gly Pro Asp Gly Arg Val Thr Gly Glu
65                  70                  75                  80

Ala Asp Val Glu Phe Ala Thr His Glu Asp Ala Val Ala Ala Met Ser
                85                  90                  95

Lys Asp Lys Ala Asn Met Gln His Arg Tyr Val Glu Leu Phe Leu Asn
            100                 105                 110

Ser Thr Ala Gly Ala Ser Gly Gly Ala Tyr Glu His Arg Tyr Val Glu
        115                 120                 125

Leu Phe Leu Asn Ser Thr Ala Gly Ala Ser Gly Gly Ala Tyr Gly Ser
    130                 135                 140

Gln Met Met Gly Gly Met Gly Leu Ser Asn Gln Ser Ser Tyr Gly Gly
145                 150                 155                 160

Pro Ala Ser Gln Gln Leu Ser Gly Gly Tyr Gly Gly Gly Tyr Gly Gly
                165                 170                 175

Gln Ser Ser Met Ser Gly Tyr Asp Gln Val Leu Gln Glu Asn Ser Ser
            180                 185                 190

Asp Phe Gln Ser Asn Ile Ala
        195

<210> SEQ ID NO 4
<211> LENGTH: 647
<212> TYPE: PRT
<213> ORGANISM: Homo sapiens
<220> FEATURE:
<221> NAME/KEY: misc_feature
<223> OTHER INFORMATION: /note="Amino acid sequence of the
      apoptin-associating filamin clones"

<400> SEQUENCE: 4

Arg Leu Arg Asn Gly His Val Gly Ile Ser Phe Val Pro Lys Glu Thr
1               5                   10                  15

Gly Glu His Leu Val His Val Lys Lys Asn Gly Gln His Val Ala Ser
            20                  25                  30

Ser Pro Ile Pro Val Val Ile Ser Gln Ser Glu Ile Gly Asp Ala Ser
```

```
            35                  40                  45
Arg Val Arg Val Ser Gly Gln Gly Leu His Glu Gly His Thr Phe Glu
        50                  55                  60

Pro Ala Glu Phe Ile Ile Asp Thr Arg Asp Ala Gly Tyr Gly Gly Leu
65                  70                  75                  80

Ser Leu Ser Ile Glu Gly Pro Ser Lys Val Asp Ile Asn Thr Glu Asp
                85                  90                  95

Leu Glu Asp Gly Thr Cys Arg Val Thr Tyr Cys Pro Thr Glu Pro Gly
                100                 105                 110

Asn Tyr Ile Ile Asn Ile Lys Phe Ala Asp Gln His Val Pro Gly Ser
                115                 120                 125

Pro Phe Ser Val Lys Val Thr Gly Glu Gly Arg Val Lys Glu Ser Ile
        130                 135                 140

Thr Arg Arg Arg Arg Ala Pro Ser Val Ala Asn Val Gly Ser His Cys
145                 150                 155                 160

Asp Leu Ser Leu Lys Ile Pro Glu Ile Ser Ile Gln Asp Met Thr Ala
                165                 170                 175

Gln Val Thr Ser Pro Ser Gly Lys Thr His Glu Ala Glu Ile Val Glu
                180                 185                 190

Gly Glu Asn His Thr Tyr Cys Ile Arg Phe Val Pro Ala Glu Met Gly
            195                 200                 205

Thr His Thr Val Ser Val Lys Tyr Lys Gly Gln His Val Pro Gly Ser
        210                 215                 220

Pro Phe Gln Phe Thr Val Gly Pro Leu Gly Glu Gly Ala His Lys
225                 230                 235                 240

Val Arg Ala Gly Gly Pro Gly Leu Glu Arg Ala Glu Ala Gly Val Pro
                245                 250                 255

Ala Glu Phe Ser Ile Trp Thr Arg Glu Ala Gly Ala Gly Gly Leu Ala
                260                 265                 270

Ile Ala Val Glu Gly Pro Ser Lys Ala Glu Ile Ser Phe Glu Asp Arg
        275                 280                 285

Lys Asp Gly Ser Cys Gly Val Ala Tyr Val Val Gln Glu Pro Gly Asp
        290                 295                 300

Tyr Glu Val Ser Val Lys Phe Asn Glu Glu His Ile Pro Asp Ser Pro
305                 310                 315                 320

Phe Val Val Pro Val Ala Ser Pro Ser Gly Asp Ala Arg Arg Leu Thr
                325                 330                 335

Val Ser Ser Leu Gln Glu Ser Gly Leu Lys Val Asn Gln Pro Ala Ser
                340                 345                 350

Phe Ala Val Ser Leu Asn Gly Ala Lys Gly Ala Ile Asp Ala Lys Val
                355                 360                 365

His Ser Pro Ser Gly Ala Leu Glu Glu Cys Tyr Val Thr Glu Ile Asp
        370                 375                 380

Gln Asp Lys Tyr Ala Val Arg Phe Ile Pro Arg Glu Asn Gly Val Tyr
385                 390                 395                 400

Leu Ile Asp Val Lys Phe Asn Gly Thr His Ile Pro Gly Ser Pro Phe
                405                 410                 415

Lys Ile Arg Val Gly Glu Pro Gly His Gly Gly Asp Pro Gly Leu Val
                420                 425                 430

Ser Ala Tyr Gly Ala Gly Leu Glu Gly Gly Val Thr Gly Asn Pro Ala
                435                 440                 445

Glu Phe Val Val Asn Thr Ser Asn Ala Gly Ala Gly Ala Leu Ser Val
450                 455                 460
```

```
Thr Ile Asp Gly Pro Ser Lys Val Lys Met Asp Cys Gln Glu Cys Pro
465                 470                 475                 480

Glu Gly Tyr Arg Val Thr Tyr Thr Pro Met Ala Pro Gly Ser Tyr Leu
                485                 490                 495

Ile Ser Ile Lys Tyr Gly Gly Pro Tyr His Ile Gly Gly Ser Pro Phe
            500                 505                 510

Lys Ala Lys Val Thr Gly Pro Arg Leu Val Ser Asn His Ser Leu His
            515                 520                 525

Glu Thr Ser Ser Val Phe Val Asp Ser Leu Thr Lys Ala Thr Cys Ala
        530                 535                 540

Pro Gln His Gly Ala Pro Gly Pro Gly Pro Ala Asp Ala Ser Lys Val
545                 550                 555                 560

Val Ala Lys Gly Leu Gly Leu Ser Lys Ala Tyr Val Gly Gln Lys Ser
                565                 570                 575

Ser Phe Thr Val Asp Cys Ser Lys Ala Gly Asn Asn Met Leu Leu Val
            580                 585                 590

Gly Val His Gly Pro Arg Thr Pro Cys Glu Glu Ile Leu Val Lys His
        595                 600                 605

Val Gly Ser Arg Leu Tyr Ser Val Ser Tyr Leu Leu Lys Asp Lys Gly
    610                 615                 620

Glu Tyr Thr Leu Val Val Lys Trp Gly His Glu His Ile Pro Gly Ser
625                 630                 635                 640

Pro Tyr Arg Val Val Pro
                645

<210> SEQ ID NO 5
<211> LENGTH: 213
<212> TYPE: PRT
<213> ORGANISM: Homo sapiens
<220> FEATURE:
<221> NAME/KEY: misc_feature
<223> OTHER INFORMATION: /note="Amino acid sequence of the
      apoptin-associating filamin clones

<400> SEQUENCE: 5

His Glu Gly Arg Gly Val Thr Gly Asn Pro Ala Glu Phe Val Val Asn
1               5                   10                  15

Thr Ser Asn Ala Gly Ala Gly Ala Leu Ser Val Thr Ile Asp Gly Pro
            20                  25                  30

Ser Lys Val Lys Met Asp Cys Gln Glu Cys Pro Glu Gly Tyr Arg Val
        35                  40                  45

Thr Tyr Thr Pro Met Ala Pro Gly Ser Tyr Leu Ile Ser Ile Lys Tyr
50                  55                  60

Gly Gly Pro Tyr His Ile Gly Gly Ser Pro Phe Lys Ala Lys Val Thr
65                  70                  75                  80

Gly Pro Arg Leu Val Ser Asn His Ser Leu His Glu Thr Ser Ser Val
                85                  90                  95

Phe Val Asp Ser Leu Thr Lys Ala Thr Cys Ala Pro His His Gly Ala
            100                 105                 110

Pro Gly Pro Gly Pro Ala Asp Ala Ser Lys Val Val Ala Lys Gly Leu
        115                 120                 125

Gly Leu Ser Lys Ala Tyr Val Cys His Lys Ser Ser Phe Thr Val Asp
    130                 135                 140

Cys Ser Lys Ala Cys Ile Ile Met Leu Leu Val Gly Val His Gly Pro
145                 150                 155                 160
```

-continued

```
Trp Thr Pro Cys Asp Glu Ile Leu Val Lys Ala Arg Gly Gln Pro Ala
            165                 170                 175

Leu Gln Arg Val Leu Thr Cys Phe Lys Asp Lys Gly Glu Val His Thr
            180                 185                 190

Gly Gly Gln Asn Gly Gly Asp Tyr Gln Ile Pro Cys Lys Pro Leu Pro
            195                 200                 205

Leu Cys Gly Cys Pro
            210

<210> SEQ ID NO 6
<211> LENGTH: 213
<212> TYPE: PRT
<213> ORGANISM: Homo sapiens
<220> FEATURE:
<221> NAME/KEY: misc_feature
<223> OTHER INFORMATION: /note="Amino acid sequence of the
      apoptin-associating filamin clones
<221> NAME/KEY: variation
<222> LOCATION: (136)..(213)
<223> OTHER INFORMATION: Xaa can be any amino acid

<400> SEQUENCE: 6

His Glu Gly Arg Pro Thr Glu Pro Gly Asn Tyr Ile Ile Asn Ile Lys
1               5                   10                  15

Phe Ala Asp Gln His Val Pro Gly Ser Pro Phe Ser Val Lys Val Thr
            20                  25                  30

Gly Glu Gly Arg Val Lys Glu Ser Ile Thr Arg Arg Arg Arg Ala Pro
            35                  40                  45

Ser Val Ala Asn Val Gly Ser His Cys Asp Leu Ser Leu Lys Ile Pro
        50                  55                  60

Glu Ile Ser Ile Gln Asp Met Thr Ala Gln Val Thr Ser Pro Ser Gly
65                  70                  75                  80

Lys Thr His Glu Ala Glu Ile Val Glu Gly Glu Asn His Thr Tyr Cys
                85                  90                  95

Ile Arg Phe Val Pro Ala Glu Met Gly Thr His Thr Val Ser Val Lys
            100                 105                 110

Tyr Lys Gly Gln His Val Pro Gly Ser Pro Phe Gln Phe Thr Val Gly
            115                 120                 125

Pro Leu Gly Glu Gly Gly Ala His Xaa Val Arg Ala Gly Gly Pro Gly
            130                 135                 140

Leu Xaa Lys Ser Ser Trp Ser Ala Ser Arg Ile Gln Tyr Leu Gly Pro
145                 150                 155                 160

Gly Lys Leu Val Leu Glu Ala Trp Pro Leu Leu Ser Xaa Ala Pro Ala
            165                 170                 175

Xaa Leu Xaa Ser Leu Leu Arg Thr Ala Arg Thr Ala Pro Val Val Leu
            180                 185                 190

Leu Met Leu Val Xaa Glu Pro Ser Asp Xaa Asn Pro Xaa Gln Val Ser
            195                 200                 205

Thr Lys Glu His Xaa
            210

<210> SEQ ID NO 7
<211> LENGTH: 17
<212> TYPE: DNA
<213> ORGANISM: Artificial Sequence
<220> FEATURE:
<221> NAME/KEY: misc_feature
<223> OTHER INFORMATION: /note="pACT-specific 17-mer"
```

-continued

```
<221> NAME/KEY: misc_feature
<223> OTHER INFORMATION: Description of Artificial Sequence: primer

<400> SEQUENCE: 7
taccactaca atggatg                                                        17
```

METHODS AND MEANS FOR INDUCING APOPTOSIS BY INTERFERENCE IN RNA PROCESSING

The present invention relates to the field of apoptosis, as well as to the field of cancer diagnosis and treatment and diagnosis and treatment of auto-immune diseases and other diseases. In particular the invention relates to improved methods and means for inducing apoptosis in cells to be eliminated. In particular the invention relates to novel means and methods for inducing apoptosis by interfering with the RNA processing machinery of a cell. In particular it relates to inhibiting or modifying the function of RNA-protein complexes involved in RNA processing such as snRNPs and hnRNP's. Both complexes are shown herein to be components of the apoptotic pathway that can be induced by chicken anemia virus proteins VP2 and/or VP3 (also called apoptin), both the hnRNP-like and snRNPs compounds are shown to associate to CAV-derived proteins Apoptin and VP2, which both are known to be involved in the apoptotic process. Apoptin and VP2 as stated, are proteins originally found in chicken anemia virus (CAV; Noteborn et al., 1991; apoptin was originally called VP3. The apoptotic activity of these proteins was discovered by the group of the present inventors (Noteborn et al., 1994, 1997).

Apoptosis is an active and programmed physiological process for eliminating superfluous, altered or malignant cells (Earnshaw, 1995, Duke et al., 1996). Apoptosis characterized by shrinkage of cells, segmentation of the nucleus, condensation and cleavage of DNA into domain-sized fragments, in most cells followed by internucleosomal degradation. The apoptotic cells fragment into membrane-enclosed apoptotic bodies. Finally, neighbouring cells and/or macrophages will rapidly phagocytose these dying cells (Wyllie et al., 1980, White, 1996). Cells grown under tissue-culture conditions and cells from tissue material can be analysed for being apoptotic with agents staining DNA, as e.g. DAPI, which stains normal DNA strongly and regularly, whereas apoptotic DNA is stained weakly and/or irregularly (Noteborn et al., 1994, Telford et al., 1992).

The apoptotic process can be initiated by a variety of regulatory stimuli (Wyllie, 1995, White 1996, Levine, 1997). Changes in the cell survival rate play an important role in human pathogenesis, e.g. in cancer development, which is caused by enhanced proliferation but also by decreased cell death (Kerr et al., 1994, Paulovich, 1997) A variety of chemotherapeutic compounds and radiation have been demonstrated to induce apoptosis in tumor cells, in many instances via wild-type p53 protein (Thompson, 995, Bellamy et al., 1995, Steller, 1995, McDonell et al., 1995).

Many tumors, however, acquire a mutation in p53 during their development, often correlating with poor response to cancer therapy. Transforming genes of tumorigenic DNA viruses inactivate p53 by directly binding to it (Teodoro, 1997). An example of such an agent is the large T antigen of the tumor DNA virus SV40. For several (leukemic) tumors, a high expression level of the proto-oncogene Bcl-2 or Bcr-abl is associated with a strong resistance to various apoptosis-inducing chemotherapeutic agents (Hockenberry 994, Sachs and Lotem, 1997).

For such cancers (representing more than half of the tumors) alternative anti-tumor therapies are under development based on induction of apoptosis independent of p53 (Thompson 1995, Paulovich et al., 1997). One has to search for the factors involved in induction of apoptosis, which do not need p53 and/or can not be blocked by Bcl-2/Bcr-abl-like anti-apoptotic activities. These factors might be part of a distinct apoptosis pathway or being (far) downstream to the apoptosis inhibiting compounds.

Apoptin is a small protein derived from chicken anemia virus (CAV; Noteborn and De Boer, 1995, Noteborn et al., 1991, Noteborn et al, 1994), which can induce apoptosis in human malignant and transformed cell line, but not in untransformed human cell lines. In vitro, apoptin fails to induce programmed cell death in normal lymphoid dermal, epidermal, endothelial and smooth-muscle cells. However, when normal cells are transformed they become susceptible to apoptosis by apoptin. (Danen-van Ooschot, 1997 and Noteborn, 1996). Long-term expression of apoptin in normal human fibroblasts revealed that apoptin has no toxic or transforming activity in these cells.

In normal cells, apoptin was found predominantly in the cytoplasm, whereas in transformed or malignant cells i.e. characterized by hyperplasia, metaplasia or dysplasia, it was located in the nucleus, suggesting that the localization of apoptin is related to its activity (Danen-van Oorschot et al. 1997).

Apoptin-induced apoptosis occurs in the absence of functional p53 (Zhuang et al., 1995a), and cannot be blocked by Bcl-2, Bcr-abl (Zhuang et al., 199S), the Bcl-2-associating protein BAG-1 and not by the caspase-inhibitor cowpox protein CrmA (Danen-Van Oorschot, 1997a, Noteborn, 1996).

Therefore, apoptin is a potent agent for the destruction of tumor cells, or other hyperplasia, metaplasia or dysplasia which have become resistant to (chemo)therapeutic induction of apoptosis, due to the lack of functional p53 and (over)-expression of Bcl-2 and other apoptosis-inhibiting agents (Noteborn et al., 1997).

The fact that apoptin does not induce apoptosis in normal transformed human cells, at least not in vitro, suggests that a toxic effect of apoptin treatment in vivo will be very low. Noteborn et al. (1997) have provided evidence that adenovirus expressed apoptin does not have an acute toxic effect in vivo. In addition, in nude mice it was shown that apoptin has a strong anti-tumor activity.

It appears, that even pre-malignant, minimally transformed cells, may be sensitive to the death-inducing effect of apoptin. In addition, Noteborn and Zhang (1997) have shown that apoptin-induced apoptosis can be used as diagnosis of cancer-prone cells and treatment of cancer-prone cells.

Knowing that apoptin is quite safe in normal cells, but that as soon as a cell becomes transformed and/or immortalized (the terms may be used interchangeable herein) the present inventors designed novel menans and methoids for induction of apoptosis based on the identification of compounds involved in the apoptin-induced apoptotic cascade. These compounds are factors of an apoptosis pathway, which is specific for transformed cells, Therefore, these proteins are very important compounds in new treatments and diagnosis for diseases related with aberrancies in the apoptotic process, such as cancer, and (auto-)immune diseases.

A group of proteins found to be associated with apoptin is the family of hnRNP-like proteins.

The invention provides an apoptin-associating hnRNP-like protein, which is needed for RNA processing. When apoptin associates with such proteins it interferes with normal RNA processing, thus leading to apoptosis.

The invention thus further provides a method for inducing apoptosis through interference with hnRNP-like proteins (interchangeably referred to as hnRNP or hnRNP-like proteins) or other parts of hnRNP's.

The invention provides an anti-tumor therapy based on the interference with hnRNP-like proteins or other parts of hnRNP's.

As an additional mechanism hnRNP can shuttle apoptin or apoptin-like compounds to the nucleus where these compounds can induce apoptosis.

The invention thus provides hnRNP as mediator of apoptin-induced apoptosis, which is tumor-specific.

The present inventors have also shown a colocalization of VP2 with snRNP's another compound also involved in RNA processing.

The invention provides a VP2-associating snRNP-like protein or component which Is needed for RNA processing The invention further provides a method for inducing apoptosis through interference with snRNP-like Proteins or components (interchangeably referred to as snRNP or snRNP-like proteins).

The invention provides an anti-tumor therapy based on the interference with snRNP-like proteins. The invention provides snRNP as mediator of VP2-induced apoptosis.

The invention further provides a method for inducing apoptosis through interference with hnRNP-like and snRNP-like proteins.

The invention provides an anti-tumor therapy based on the interference with either or both snRNP- and hnRNP-like proteins.

The invention provides hnRNP and snRNP as mediators of VP2-induced apoptosis.

More in detail the invention provides a recombinant and/or isolated nucleic acid molecule encoding a member of the family of hnRNP proteins involved in RNA processing comprising at least a functional part of the sequence of FIG. 1 or a sequence having at least 60, preferably 70, preferably 80, more preferably 90% homology with said sequence. In cells where a particular hnRNP is not used for RNA processing such hnRNP activity can be used to shuttle apoptotic agents such as apoptin to the nucleus. It is then preferred to have such activity in an expression vector. hnRNP (-like) activity is defined as any molecule directly or indirectly providing the same kind of activity as an hnRNP or an hnRNP-like protein.

Such a vector preferably also encodes apoptotic activity, preferably apoptin-like activity which is defined analogous to hnRNP-like activity.

In this definition functional equivalents and/or fragments of apoptin are also encompassed.

In the case where hnRNP's are involved in RNA processing these compounds can be inhibited by apoptin-like activity, but also by for instance antisense molecules for hnRNP components. The invention thus also provides a recombinant and/or isolated nucleic acid molecule encoding an antisense recombinant molecule which can hybridize with a recombinant acid molecule according to claim 1. Preferably again such a molecule is present in an expression vector.

Apoptosis is preferably induced in a gene therapy setting, so that it is preferred to deliver all vectors to cells making use of gene delivery vehicle. Gene delivery vehicle are known in the art and our capable of transporting nucleic acid molecules of interest to cells. They include recombinant viruses (such as adenoviruses and retroviruses) as well as polymers and liposomes and the like.

It is preferred to also block the snRNP involvement in RNA processing. This can be done by VP2 (or VP2-like activity (same definition as hnRNP-like activity)) or by a further antisense molecule hybridizing with a nucleic acid molecule encoding a snRNP component.

Both options are provided by the present invention. The invention thus provides an expression vector encoding an antisense molecule for a nucleic acid encoding a component of an snRNP, preferably together with an hnRNP antisense molecule.

The invention also provides a method for identifying apoptotic agents comprising the use of nucleic acid molecules encoding members of the hnRNP-like family and the snRNP-like family.

Apoptotic agents identified by such a route are also considered part of this invention. These agents will typically be hnRNP antagonists or snRNP antagonists of which apoptin and VP2 are the first examples.

The most preferred method of inducing apoptosis is using antagonists to both snRNP and hnRNP, but often singel antagonists will suffice.

The invention will be explained in more detail in the following experimental part. This only serves for the purpose of illustration and should not be interpreted as a limitation of the scope of the invention.

EXPERIMENTAL PART

The inventors have used the yeast-2 hybrid system (Durfee et al., 1993) to identify apoptin-associating cellular compounds, that are essential in the induction of apoptosis. The used system is an in-vivo, strategy to identify human proteins capable of physically associating with apoptin. It has been used to screen cDNA libraries for clones encoding proteins capable of binding to a protein of interest (Fields and Song, 1989, Yang et al., 1992).

Construction of pGBT9-VP3

For the construction of the bait plasmid, which enables the identification of apoptin-associating proteins by means of a yeast-two-hybrid system, plasmid pET-16b-VP3 (Noteborn, unpublished results) was treated with NdeI and BamHI. The 0.4 kb NdeI-BamHI DNA fragment was isolated from low-melting-point agarose.

Plasmid pGBT9 (Clontech Laboratories, Inc, Palo Alto, USA) was treated with the restriction enzymes EcoRI and BamHI. The about 5.4 kb DNA fragment was isolated and ligated with an EcoRI-NdeI linker and 0.4-kb NdeI-BamHI DNA fragment containing the apoptin-encoding sequences starting from its own ATG-initiation codon. The final construct containing a fusion gene of the GAL4-binding domain sequence and apoptin under the regulation of the yeast promoter ADH was called pGBT-VP3 and was proven to be correct by restriction-enzyme analysis and DNA-sequencing according to the Sanger method (1977).

All cloning steps were essentially carried out as described by Maniatis et al. (1992). The plasmid pGBT-VP3 was purified by centrifugation in a CcCl gradient and column chromatography in Sephacryl S500 (Pharmacia).

GAL4-activation Domain-tagged cDNA Library

The expression vector pACT, containing the cDNAs from Epstein-Bar-virus-transformed human B cells fused to sequences for the GAL4 transcriptional activation domain, was used for detecting apoptin-associating proteins. The pACT c-DNA library is derived from the lambda-ACT cDNA library, as described by Durfee et al. 1993.

Bacterial and Yeast Strains

The *E. coli* strain JM109 was the transformation recipient for the plasmid pGBT9 and pGBT-VP3. The bacterial strain Electromax/DH10B was used for the transformation needed for the recovery the apoptin-associating pACT-cDNAs, and was obtained from GIBCO-BRL, USA.

The yeast strain Y190 was used for screening the cDNA library, and all transformations which are part of the used yeast-two-hybrid system.

Media

For drug selections Luria Broth (LB) plates for *E. coli* were supplemented with ampicillin (50 microgram per ml). Yeast YPD and SC media were prepared as described by Rose et al. (1990), Transformation of Competent Yeast Strain Y190 with Plasmids pGBT-VP3 and pACT-cDNA and Screening for Beta-galactosidase Activity The yeast strain Y190 was made competent and transformed according to the methods describe by Klebe et al. (1983). The yeast cells were first transformed with pGBT-VP3 and subsequently transformed with pACT-cDNA, and these transformed yeast cells were grown on histidine-minus plates, also lacking leucine and tryptophan.

Hybond-N filters were layed on yeast colonies, which were histidine-positive and allowed to wet completely. The filters were lifted and submerged in liquid nitrogen to permeabilize the yeast cells. The filters were thawed and layed with the colony side up on Whattman 3 MM paper in a petridish with Z-buffer (Per liter: 16.1 gr $Na_2HPO_4.7H_2O$, 5.5 gr $NaH_2PO_4.H_2O$, 0.75 gr KCl and 0,246 gr $MgSO_4.7H_2O$, pH 7.0) containing 0.27% beta-mercaptoethanol and 1 mg/ml X-gal. The filters were incubated for at least 15 minute or during night.

Recovery of Plasmids from Yeast

Total DNA from yeast cells, which were histidine- and beta-galactosidase-positive was prepared by using the glusulase-alkaline lysis method as described by Hoffman and Winston (1987) and used to transform Electromax/DH10B bacteria via electroporation using a Bio-Pad Genepulser according the manufacturers specifications.

Transformants were plated on LB media containing ampicillin.

Isolation of Apoptin-associating pACT Clones

By means of colony-filter assay the colonies were lysed and hybridized to a radioactive-labeled 17-mer oligomer, which is specific for pACT (see also section Sequence analysis).

Plasmid DNA was isolated from the pACT-positive clones, and by means of XhoI digestion analysed for the presence of a cDNA insert.

Sequence Analysis

The subclones containing the sequence encoding apoptin-associating proteins were sequenced using dideoxy NTP's according to the Sanger method which was performed by Eurogentec, Nederland BV (Maastricht, The Netherlands). The sequence primer used was a pACT-specific 17-mer comprising of the DNA-sequence 5'-TACCACTACAATGGATG-3' (SEQ. ID NO: 7).

The sequences of the apoptin-associating proteins were compared with known gene sequences from the EMBL/(Genbank.

Results and Discussion

Apoptin induces specifically apoptosis in transformed cells, such as cell lines derived from human tumors. To identify the essential compounds in this cell-transformation-specific and/or tumor-specific apoptosis pathway, a yeast genetic screen was carried out.

We have used a human cDNA library, which is based on the plasmid vector pACT containing the complete cDNA copies made from Epstein-Barr virus-transformed human B cells (Durfee et al., 1993).

Construction of a Bait Plasmid Expressing a Fusion Gene Product of GAL4-DNA-binding Domain and Apoptin To examine the existence of apoptin-associating proteins by the human transformed/tumorigenic cDNA library, a so-called bait plasmid had to be constructed.

To that end, the complete apoptin-encoding region, flanked by about 40 basepairs downstream from the apoptin gene, was cloned in the multiple cloning site of plasmid pGBT9.

The final construct, called pGBT-VP3, was analysed by restriction-enzyme analysis and sequencing of the fusion area between apoptin and the GAL4-DNA-binding domain.

A Gene(Fragment) Encoding an Apoptin-associating Protein is Determined by Transactivation of a GAL4-responsive Promoter in Yeast The apoptin gene is fused to the GAS4-DNA-binding domain of plasmid pGBT-VP3, whereas all cDNAs derived from the transformed human B cells are fused to the GAL4-activation domain of plasmid pACT. If one of the cDNAs will bind to apoptin, the GAL4-DNA-binding domain will be in the vicinity of the GAL4-activation domain resulting in the activation of the GAL4-responsive promoter, which regulates the reporter genes HIS3 and LacZ.

The yeast clones containing plasmid expressing apoptin and a plasmid expressing an apoptin-associating protein (fragment) can grow on a histidine-minus medium and will stain blue in a beta-galactosidase assay. Subsequently, the plasmid with the cDNA insert encoding the apoptin-associating protein can be isolated and characterized.

Before we could do so, however, we have determined that transformation of yeast cells with pGBT-VP3 plasmid only or in combination with an empty pACT vector, did not result in the activation of the GAL4-responsive promoter.

Identification of Apoptin-associating Proteins Coded by cDNAs Derived from a Human Transformed B Cell Line We have found yeast colonies, which upon transformation with pGBT-VP3 and pACT-CDNA were able to grow a histidine-minus medium (also lacking leucine and tryptophan) and stained blue in a beta-galactosidase assay. These results indicate that these yeast colonies contain besides the bait plasmid pGBT-VP3 a pACT plasmid encoding for a potential apoptin-associating protein.

Plasmid DNA was isolated from these positive yeast colonies, which were transformed in bacteria. By means of an filter-hybridization assay using a pACT-specific labeled DNA-probe, the clones containing pACT plasmid could be determined. Subsequently, pACT DNA was isolated and digested with restriction enzyme XhoI, which is indicative for the presence of a cDNA insert. Finally, the pACT plasmids with a cDNA insert were sequenced.

Description of Apoptin-associating Proteins

The yeast genetic screen for apoptin-associating proteins resulted in the detection of a human homolog of the hnRNP- H. The determined DNA sequence is shown in SEQ ID NO: 1 in the sequence listing contained herein. The amino acid sequence of the cloned hnRNP-H homolog is shown in SEQ ID NO: 2 in the sequence listing contained herein. Most likely, the cloned cDNA insert represents a new member of the family of (human) hnRNPs.

Characteristics of hnRNP-H

The detected cDNA shows homology to part of hnRNP-H, which is the abbreviation of heterogenous nuclear ribonucleoprotein H). hnRNPs bind to primary RNA transcripts (hnRNA or pre-mRNA), and are among the most abundant proteins in the nucleus. More than 20 hnRNPs have been discovered so far, differing in size, localization, domains and nucleic acid binding specificity, Some hnRNPs were found to be confined to the nucleus, whereas others shuttle between the nucleus and cytoplasm (Dreyfuss et al., 1993).

Antibody staining shows a general nucleoplasmic localization, with little staining in nucleoli and electron-microscopy analysis localized hnRNPs, mainly to perichromatin fibrils. There is no evidence for free (not RNA-bound) hnRNPs in the nucleus. Many hnRNPs show preferential binding to certain RNA sequences, like stretches of identical bases or intron-splice sites. Almost all, including hnRNP-H have a common domain with which they can bind to RNA (Holzmann et al., 1997, Dreyfuss et al., 1993).

The Relationship Between hnRNP-like Proteins and Apoptin

The hnRNP-H protein interacts with the proteins CBP80 and CBP20, the components of the nuclear cap-binding complex.

The hnRNP-H protein is closely related to hnRNP, which also binds to mentioned CBPs (Gamberi et al., .1997). Apoptin association will result in the inhibition of hnRNP activity, In this respect, it is interesting to mention that the CAV thereby developed a strategy, which makes the translation of the capsid protein cap-independent. Synthesis of VP2 and apoptin preceeds the production of the virus capsid protein. Most likely, apoptin will cause inhibition of capping activity by interference with hnRNP-H Noteborn et al., 1991).

Upon various signals the expression of hnRNP-H can be up-regulated in transformed fibroblasts but not in normal cells (Honore et al., 1995). This seems to correlate with the apoptin activity in (human) transformed cells, whereas it does not in various normal human cells.

Interestingly, immunofluorescence-microscopy revealed that hnRNP are concentrated in discrete regions of the nucleoplasm, in contrast to the general nucleoplasmic distribution of previously characterized hnRNP (Matunis et al., 1994).

Co-localization studies in transformed human fibroblasts and keratinocytes with apoptin-specific and hnRNP-H monoclonal antibodies proved that apoptin is situated in a similar nuclear structure.

Thusfar, hnRNP-H proteins were not linked with the apoptotic pathway. We provide evidence (apoptin as an example) that interference with the function of hnRNP-H results in the induction of apoptosis.

Co-localization of VP2 and snRNPs

Noteborn et al. (1997) have provided evidence that the other CAV-derived VP2 protein induces relatively weakly apoptosis in comparison to apoptin. Interestingly, however, VP2 has an enhancing effect on apoptin-induced apoptosis.

VP2 is like apoptin present in distinct structures in the nucleus. The structures of apoptin do not co-loxcalize with these of VP2. We have examined to which structures VP2 belong. Co-localization studies with an apoptin-specific and a snRNP-specific monoclonal antibody clearly revealed co-localization of snRNPs and VP2. In a parallel control experiment, it was proven that apoptin did not co-localize with snRNPs.

We have shown that the observed VP2 and apoptin activities, and their interactive behaviour, can be explained by the fact that both VP2 and apoptin interfere in the RNA processing pathway.

It is the first time that such a dualism of interference within the apoptotic pathway is linked to the apoptotic process.

Conclusions

In conclusion, we have provided evidence that interference of specific factors with RNA processing, to be precise hnRNP-like proteins and/or snRNP-like proteins, will result in induction of apoptosis.

Therapies based on induction of apoptosis are possible if they succeed in the interference with the function of hnRNP-like and/or snRNP-like proteins. Examples of such interfering RNA-processing proteins are the CAV-derived proteins VP2 and apoptin.

Other Apoptin-associating Proteins

The genetic yeast screen with pGBT-VP3 as bait plasmid and pACT plasmid containing cDNAs from transformed human B cells also delivered the protein filamin. The protein filamin is localized within lamellipodia and filopodia. Filamin is one of the cross-linking proteins of actin. It may play an additional role of linking the cytoskeleton to cell-substratum adhesion Sites (Matsudaira, 1994). Two independent filamin-like clones were found. The found associating amino acid sequence of the two filamin clones are shown in FIG. 3.

REFERENCES

1. Bellamy, C. O. C., Malcornson, R. D. G., Harrison, D. J., and Wyllie, H. 1995. Cell death and disease: The biology and regulation of apoptosis. Seminare in Cancer Biology 6, 3–12.
2. Danen-Van Oorschot, A. A. A. M., Fischer, D., Grimbergen, J. M., Klein, B., Zhuang, S.-M., Falkenburg, J. H. F., Backendorf, C., Quax, P. H. A., Van der Eb, J. A., and Noteborn, M. H. M. (1997), Proceedings National Academy Sciences, USA: 94, 5843–5847.
3. Danen-Van Oorschot, A. A. A. M, Den Hollander A., Takayama, S., Reed, J., Van der Eb, A. J. and Noteborn, M. H. M. (1997a). BAG-1 inhibits p53-induced but not apoptin-induced apoptosis, Apoptosis 2, 395–402.
4. Dreyfuss, G., Matunis, M. J., Pinol-Roma, S., and Burd, C. G. (1993). HnRNP proteins and the biogenesis of mRNA. Annual Review Biochemistry 62, 299–321.
5. Duke, R. C., Ocjius, D. M, Young, J, D-E. (1996). Cell suicide in health and disease. Scientific American December 1996, 48–55.
6. Durfee, T., Becherer, K., Chen, P.-L., Yeh, S.-H., Yang, Y., Kilburn, A. E., Lee, W.-H., and Elledge, S. J. (1993). The retinoblastoma protein associates with the protein phosphate type I catalytic subunit. Genes and Development 7, 555–569.
7. Barnshaw, W. C., 1995. Nuclear changes in apoptosis. Current Opinion in Cell Biology 7, 337–343.

8. Fields, S. and Song, O. K. (1989). A novel genetic system to detect protein-protein interactions. Nature 340, 245–246.
9. Gamberi, C., Izaurralde, E., Beisel, C., and Mattaj, I. W. (1997), Interaction between the human nuclear cap-binding protein complex and hnRNP F.
10. Hockenberry, D. M. (1994). Bcl-2 in cancer development and apoptosis. Journal of Cell Science, Supplement 16, 51–55.
11. Hoffman, C. S. and Winston, F. (1987). A ten-minute DNA preparation from yeast efficiently releases autonomous plasmids for transformation of Escherichia coil. Gene 57, 267–272.
12. Holzmann, K., Korosec, T., Gerner, C., Grimm, R., Sauermann, G. (1997). European Journal Biochemistry 244, 479–486.
13. Honore, B., Rasmussen, H. H., Vorum, H., Deigaard, K., Liu, X., Gromov, P., Madsen, P., Gesser, B., Tommerup, N., and Celis, J. E. (1995). Journal of Biological Chemistry 270, 28780–28789.
14. Kerr, J. F. R., Winterford, C. M., and Harmon, B. V. (1994). Apoptosis: It significance in cancer and cancer therapy. Cancer 73, 2013–2026.
15. Klebe, R. J., Harriss, J. V., Sharp, Z. D., and Douglas, M. G. (1983), A general method for polyethylene-glycol-induced genetic transformation of bacteria and yeast. Gene 25, 333–341.
16. Levine, A. J. (1997). p53, the cellular gate keeper for growth and division. Cell 88, 323–331.
17. Maniatis, T., Fritsch, E. P., and Sambrook, J. (1982). Molecular Cloning: A Laboratory Manual. CSHL Press, New York, USA.
18. Matunis, M. J., Xing, J., Dreyfuss, G. (19 4). The HNRNP-F protein: unique primary structure, nucleic acid-binding properties, and subcellular localization. Nucleic Acids Research 22, 1059–1067.
19. McDonell T. J., Meyn, R. E., Robertson, L. E. (1995). Implications of apoptotic cell death regulation in cancer therapy. Seminars in Cancer Biology 6, 53–60.
20. Noteborn, M. H. M. (1996). PCT application WO 96/41191. Apoptin induces apoptosis in human transformed and malignant cells but not in normal cells as essential characteristic for the development of an anti-tumor therapy.
21. Noteborn, M. H. M., and De Boer, G. F. (1996). U.S. Pat. No. 030, 335.
22. Noteborn, M. H. M., De Boer, G. F,, Van Roozelaar, D., Karreman, C., Kranenburg, O., Vos, J., Jeurissen, S., Zantema, A., Hoeben, R., Koch, G., Van Ormondt, H., and Van der Eb, A. J. (1991). Characterization of cloned chicken anemia virus DNA that contains all elements for the infectious replication cycle. Journal of Virology 65, 3131–3139.
23. Noteborn, M. H. M., Hoeben, R.C ., and Pietersen, A. (1997). A gene delivery vehicle expressing the apoptosis-inducing proteins VP2 and/or apoptin. European Patent Application no. 97201121.7
24. Noteborn, M. R. M., Todd, D., Verachueren, C. A. J., De Gauw, H. W. F. M., Curran, W. L., Veldkamp, S., Douglas, A. J., McNulty, M. S., Van der Eb, A. J., and Koch, G. (1994). A single chicken anemia virus protein induces apoptosis. Journal of Virology 68, 346–351.
25. Noteborn, M. H. M., and Zhang, Y. (1997). Methods and means for determining the transforming capability of agents, for determining the predisposition of cells to become transformed and prophylactic treatment of cancer using apoptin-like activity. European Patent Application no. 97439
26. Paulovich, A. G., Toczyski, D., Hartwell, (1997). When checkpoints fail. Cell 88, 315–321.
27. Rose, M. D., Winston, F., and Hieter, P. (1990). Methods in yeast genetics. A laboratory course manual. Cold Spring Harbor Laboratory Press, Cold Spring Harbor, N.Y., USA.
28. Sachs, L. and Lotem, J. (1993). Control of programmed cell death in normal and leukemia cells: New implications for therapy. Blood 82, 15–21.
29. Sanger, F., Nicklen, S., and Couleen, A. R. (1977). DNA sequencing with chain-terminating inhibitors. Proceedings National Academic Sciences USA 74, 5463–5467.
30. Steller, H. (1995). Mechanisms and genes of cellular suicide. Science 267, 1445–1449.
31. Telford, W. G., King, L. E., Fraker, P. J. (992). Comparative evaluation of several DNA binding dyes in the detection of apoptosis-associated chromatin degradation by flow cytometry. Cytometry 13, 137–143.
32. Teodoro, J. G. and Branton, P. E. (1997). Regulation of apoptosis by viral gene products. Journal of Virology 71, 1739–1746.
33. Thompson, C. B, (1995). Apoptosis in the pathogenesis and treatment of disease. Science 267, 1456–1462.
34. White, E. (1996). Life, death, and the pursuit of apoptosis. Genes and development 10, 1–15.
35, Wyllie, A. H. (1995). The genetic regulation of apoptosis. Current Opinion in Genetics and Development 5, 97–104.
36. Wyllie, A. H., Kerr, J. F. R., Currie, A. R. (1980). Cell death; The significance of apoptosis. International Review of Cytology 68, 251–306.
37. Yang, X., Hubbard, E. J. A., and Carlson, M. (1992). A protein kinase substrate identified by the two-hybrid system. Science 257, 680–682.
38. Zhuang, S.-M., Landegent, J. E., Verscbueren, C. A. J., Falkenburg, J. H. F., Van Ormondt, H., Van der Eb, A. J., Noteborn, M. H. M. (1995). Apoptin, a protein encoded by chicken anemia virus, induces cell death in various human hematologic malignant cells in vitro. Leukemia 9 S1, 118–120.
39. Zhuang, S.-M., Shvarts, A., Van Ormondt, H., Jochemsen, A.-G., Van der Eb, A. J., Noteborn, M. H. M. (1995). Apoptin, a protein derived from chicken anemia virus, induces a p53-independent apoptosis in human osteosarcoma cells. Cancer Research 55, 486–489.

What is claimed is:

1. A recombinant and/or isolated nucleic acid molecule encoding a member of the family of hnRNP proteins involved in RNA processing, said recombinant and/or isolated nucleic acid molecule comprising:

the sequence of SEQ ID NO: 1.

2. An expression vector comprising a recombinant and/or isolated nucleic acid molecule encoding a member of the family of hnRNP proteins involved in RNA processing, said recombinant and/or isolated nucleic acid molecule comprising:

the sequence of SEQ ID NO: 1.

3. An expression vector comprising:

a nucleic acid sequence encoding apoptin, and a recombinant and/or isolated nucleic acid molecule encoding a member of the family of hnRNP proteins involved in RNA processing, said recombinant and/or isolated nucleic acid molecule comprising the sequence of SEQ ID NO:1.

4. A recombinant and/or isolated nucleic acid molecule encoding an antisense recombinant molecule which is completely complementary to the nucleic acid molecule of SEQ ID NO: 1.

5. An expression vector comprising an isolated nucleic acid molecule encoding an antisense recombinant molecule which is completely complementary to the nucleic acid molecule of SEQ ID NO: 1.

6. A gene delivery vehicle comprising the expression vector of claim 5.

7. A gene delivery vehicle comprising:

an expression vector comprising a recombinant and/or isolated nucleic acid molecule encoding a member of the family of hnRNP proteins involved in RNA processing, said recombinant and/or isolated nucleic acid molecule comprising:

the sequence of SEQ ID NO: 1.

8. A gene delivery vehicle comprising:

a nucleic acid sequence encoding apoptin, and an expression vector comprising a recombinant and/or isolated nucleic acid molecule encoding a member of the family of hnRNP proteins involved in RNA processing, said recombinant and/or isolated nucleic acid molecule comprising the sequence of SEQ ID NO: 1.

9. A recombinant and/or isolated nucleic acid molecule encoding a member of the family of hnRNP proteins involved in RNA processing, said recombinant and/or isolated nucleic acid molecule comprising a sequence encoding the member of SEQ ID NO:2.

10. An expression vector comprising a recombinant and/or isolated nucleic acid molecule encoding a member of the family of hnRNP proteins involved in RNA processing, said recombinant and/or isolated nucleic acid molecule comprising a sequence encoding the member of SEQ ID NO:2.

11. The expression vector of claim 10, further comprising a nucleic acid sequence encoding apoptin.

12. A recombinant and/or isolated nucleic acid molecule encoding an antisense recombinant molecule which is completely complementary to a nucleic acid molecule encoding the hnRNP protein of SEQ ID NO:2.

13. An expression vector comprising an isolated nucleic acid molecule encoding an antisense recombinant molecule which is completely complementary to a nucleic acid molecule encoding the hnRNP protein of SEQ ID NO:2.

14. A gene delivery vehicle comprising the expression vector of claim 13.

15. A gene delivery vehicle comprising:

an expression vector comprising a recombinant and/or isolated nucleic acid molecule encoding a member of the family of hnRNP proteins involved in RNA processing, said recombinant and/or isolated nucleic acid molecule comprising: a sequence encoding the member of SEQ ID NO:2.

16. The gene delivery vehicle of claim 15, further comprising a nucleic acid sequence encoding apoptin.

* * * * *